United States Patent
Abrahmsén et al.

(10) Patent No.: US 6,723,553 B2
(45) Date of Patent: Apr. 20, 2004

(54) PROMOTER SEQUENCES

(75) Inventors: Lars Abrahmsén, Bromma (SE); Jonas Ekblom, Uppsala (SE); Margareta Forsgren, Stockholm (SE); Jan Hörling, Lidingö (SE); Per Johansson, Kista (SE)

(73) Assignee: Biovitrum AB, Stockholm (SE)

( * ) Notice: Subject to any disclaimer, the term of this patent is extended or adjusted under 35 U.S.C. 154(b) by 0 days.

(21) Appl. No.: 09/891,711

(22) Filed: Jun. 26, 2001

(65) Prior Publication Data

US 2002/0082404 A1 Jun. 27, 2002

Related U.S. Application Data

(60) Provisional application No. 60/216,414, filed on Jul. 6, 2000.

(30) Foreign Application Priority Data

Jun. 27, 2000 (SE) ............................................. 0002417

(51) Int. Cl.[7] .............................. C12N 1/20; C12N 1/00; C12N 5/00; C07H 21/02
(52) U.S. Cl. ............................. 435/252.3; 435/320.1; 435/325; 536/24.1
(58) Field of Search ..................... 536/24.1; 435/320.1, 435/252.3, 325

(56) References Cited

FOREIGN PATENT DOCUMENTS

WO    WO 00/09677    2/2000

OTHER PUBLICATIONS

Brown et al., "The SREBP Pathway: Regulation of Cholesterol Metabolism by Proteolysis of a Membrane-Bound Transcription Factor," CELL 89:331–340 (May 2, 1997).

Brown et al., "A proteolytic pathway that controls the cholesterol content of membranes, cells, and blood," Proc. Natl. Acad. Sci. USA 96:11041–11048 (Sep. 1999).

Horton et al., "Activation of Cholesterol Synthesis in Preference to Fatty Acid Synthesis in Liver and Adipose Tissue of Transgenic Mice Overproducing Sterol Regulatory Element-binding Protein-2," Clin. Invest. 101(11):2331–2339 (Jun. 1998).

Kakuma et al., "Leptin, troglitazone, and the expression of sterol regulatory element binding proteins in liver and pancreatic islets," PNAS 97(15):8536–8541 (Jul. 18, 2000).

Nagase et al., "Prediction of the Coding Sequences of Unidentified Human Genes. III. The Coding Sequences of 40 New Genes (KIAA0081–KIAA0120) Deduced by Analysis of cDNA Clones from Human Cell Line KG–1," DNA Research 2:37–43 (1995).

Pai et al., "Differential Stimulation of Cholesterol and Unsaturated Fatty Acid Biosynthesis in Cells Expressing Individual Nuclear Sterol Regulatory Element-binding Proteins," J. Biological Chemistry 273(40):26138–26148 (1998).

Sakai et al., "Molecular Identification of the Sterol-Regulated Luminal Protease that Cleaves SREBPs and Controls Lipid Composition of Animal Cells," Molecular Cell 2:505–514 (1998).

Sheng et al., "Independent regulation of sterol regulatory element-binding proteins 1 and 2 in hamster liver," Proc. Natl. Acad. Sci. USA 92:935–938 (Feb. 1995).

Shimano et al., "Overproduction of Cholesterol and Fatty Acids Causes Massive Liver Enlargement in Transgenic Mice Expressing Truncated SREBP–1a," J. Clin. Invest. 98(7):1575–1584 (Oct. 1996).

Shimomura, "Insulin resistance and diabetes mellitus in transgenic mice expressing nuclear SREBP–1c in adipose tissue: model for congenital generalized lipodystrophy," Genes & Development 12:3182–3194 (1998).

Xu et al., "Sterol Regulatory Element Binding Protein–1 Expression Is Suppressed by Dietary Polyunsaturated Fatty Acids," J. Biological Chemistry 274(33):23577–23583 (Aug. 13, 1999).

GenBank™ Accession No. AF078105 (Nov. 19, 1998).

*Primary Examiner*—Rebecca E. Prouty
*Assistant Examiner*—Malgorzata A Walicka
(74) *Attorney, Agent, or Firm*—Fish & Richardson P.C.

(57) ABSTRACT

The present invention relates an isolated human Site-1 Protease promoter region. The invention also relates to screening methods for agents decreasing the expression of Site-1 protease and thereby being potentially useful for the treatment of medical conditions related to obesity and/or diabetes.

12 Claims, No Drawings

SEQUENCE LISTING

<160> NUMBER OF SEQ ID NOS: 6

<210> SEQ ID NO 1
<211> LENGTH: 980
<212> TYPE: DNA
<213> ORGANISM: Homo sapiens

<400> SEQUENCE: 1

```
ctccgcggcg aacacgcctg ggcactccat tcggggctgt ttactcccaa ctctcgcgag      60
actgggcggc cgggccagcg aggcccacag ctgggagcct cagctccgcc gacccagcgt     120
gccctgtctg tcccgcgctc ccggggcttg cgtgcgcgct ctgacgccg tgggcagcgg      180 gaccacgccg ggaggatgga cgaaggtgct cgcgacattt gcggcggcgg gggccggtgg    240
cagggtggaa gcggaggggc gtggccagcg agctgccagg cggcgagaac gcgctggggg    300
aacccttggt ccgctctgcg cgtcgctcta ggatccccga aaaggagcac gggcgcgaaa     360
gcggccaggc tgggccagga tctagaaaga ctgcctggcg caggctccct gccccgcgg      420 gcctgctgtc atggactcgt ggagagctcg cttcccgcgc ggacccttcc tgcagggtc     480 cacgtccagg caccggcggc tcggacaccc caccccggc cgggcacctg ccctgggtgc     540
cccttaaccc gggcggtagc tcgttaagat ggcgaagtgt ccggtccgga acacgcgaaa    600
ccccaaatcc cgcctgcccg acctcctgac ccccggcccc acgggacgac agactgggcc    660
tcccgacgcg cagcgcgctg ccgggacacc ggtgcgtgcg aaacggagga cctttgtaac     720
gccacgtgtt tgctctttt gaaaaaacaa gaataaatgt gttaaactgt ctgaaaagct     780
tgccgcctaa aagatgtctg ggtgacttag atgctaggat cagtttgttt tcaatgtaaa    840
tggaccagcc cggactccgt acggcactag caggggactg aaagcgtctt caggtactgc     900
tggtgggcgg tgatgcgcta caggccgatc agacagtttt gtgtcttctg gaacttgaca    960
ctgcaccacg gtaatgctga                                               980
```

<210> SEQ ID NO 2
<211> LENGTH: 2469
<212> TYPE: DNA
<213> ORGANISM: Homo sapiens

<400> SEQUENCE: 2

```
ttgagtctgt ctggaggctc cgggccagag cagggcgtat tgtttcactc ggtgaatgct      60
catttcacgt aaagaaaacc aggcaacgga acaagctgcc ggagcgcgca gaccccgca     120 gggccgcggt acaggcacgc tgtgtccaaa caagcgccgg aggcccgcg cccacctccc    180 ccgacccggc ccggcccccg cagccctcgc ctcggggcct cggacgcaac cggcacacct   240
```

-continued

| | |
|---|---|
| gagcgagcgg gccgccaccg ctaggcggag cgggtcgggg aggccgcgcg cgggcggctg | 300 |
| acgtacctgc gccgccggga gctcagggcc ggcgggcccg ggatgacggc gcctccgcgg | 360 |
| cgaacacgcc tgggcactcc attcgggget gtttactccc aactctcgcg agactgggcg | 420 |
| gccgggccag cgaggcccac agctgggagc ctcagctccg ccgacccagc gtgccctgtc | 480 |
| tgtcccgcgc tcccggggct tgcgtgcgcg ctctggacgc cgtgggcagc gggaccacgc | 540 |
| cgggaggatg gacgaaggtg ctcgcgacat ttgcggcggc gggggccggt ggcagggtgg | 600 |
| aagcggaggg gcgtggccag cgagctgcca ggcggcgaga acgcgctggg ggaacccttg | 660 |
| gtccgctctg cgcgtcgctc taggatcccc gaaaaggagc acgggcgcga aagcggccag | 720 |
| gctgggccag gatctagaaa gactgcctgg cgcaggctcc ctgcccccgc gggcctgctg | 780 |
| tcatggactc gtggagagct cgcttcccgc gcggacccct cctgcagggg tccacgtcca | 840 |
| ggcaccggcg gctcggacac cccacccccg gccgggcacc tgccctgggt gccccttaac | 900 |
| ccggcggta gctcgttaag atggcgaagt gtccggtccg gaacacgcga aaccccaaat | 960 |
| cccgcctgcc cgacctcctg accccggcc ccacgggacg acagactggg cctcccgacg | 1020 |
| cgcagcgcgc tgccgggaca ccggtgcgtg cgaaacggag gacctttgta acgccacgtg | 1080 |
| tttgctcttt ttgaaaaaac aagaataaat gtgttaaact gtctgaaaag cttgccgcct | 1140 |
| aaaagatgtc tgggtgactt agatgctagg atcagtttgt tttcaatgta aatggaccag | 1200 |
| cccggactcc gtacggcact agcagggac tgaaagcgtc ttcaggtact gctggtgggc | 1260 |
| ggtgatgcgc tacaggccga tcagacagtt ttgtgtcttc tggaacttga cactgcacca | 1320 |
| cggtaatgct gaactgcacc aatattacag atcacagcgc atcatcttcc ttcaacatga | 1380 |
| tttaacacag ttgacttaat atggtggata aatgtagaat cacaaattac catacccac | 1440 |
| ctcaggcttc tacttcgtaa ttttgagcag gttgtttaac ctctttgtac ctcagcttct | 1500 |
| tcattacaaa aatagggta ctagccaggc ggggtggctc cgcctgtaa tcccagcact | 1560 |
| tggggaggcc gaggcagccg gatcacttga ggtcagaagt ttcagaccag cctggtcaac | 1620 |
| atgggtgaaa cgccggctct accaaaaata taaaaactta gctgagtgtg gtagcgcatg | 1680 |
| actgtaatcc cagcaactca ggaggctgag gcagagaatc gcttgaacct gggaggcgga | 1740 |
| ggttgcagtg agctgagatc gtaccactgc actccagctt gggcgacaga gcgagactct | 1800 |
| gccttaaaaa taaataaata atttttaaaa aaatagggg tactaatatc taccttaaag | 1860 |
| gatgagggtt aaattaagta cacacataag ccctagcgca gtggcttatg cctgtaatct | 1920 |
| caacactttg ggagtctgtg gcgggaggat cacttgagcc caggagtttg agactagtct | 1980 |
| gggcaacaga gacatgtctc tatagttgtg tttggttttg tttttaccag gtgtggtggt | 2040 |
| gtgcacctgc agtcccagct actagggagg ctgaggtggg aggactgcct gagcccagga | 2100 |
| ggtcgaggct gcagtgagcc atgattgtgc cactgcactc cagcctgggc aacacagcaa | 2160 |
| gaccttgtct caaaacaaa caaaaagcat actcataaag tgctcggctc ctatatgatt | 2220 |
| caatatgtgg tggtggattc ttgaatcctt tcctgactca gatctcatac gattttctga | 2280 |
| acttttggag aatccttgcc tctctgcatt tgcaaaccgt caaaggcact cccttctgcc | 2340 |
| accacacaaa gcatttgatt ttaaacttga ctatgtcctt ctgttccaac tttaggtaaa | 2400 |
| ttaatcttgg tcagggttct ctgaacagcc ctttagtcac tatgccattg aatacatggc | 2460 |
| cctacagct | 2469 |

<210> SEQ ID NO 3
<211> LENGTH: 4338

-continued

```
<212> TYPE: DNA
<213> ORGANISM: Homo sapiens
<220> FEATURE:
<221> NAME/KEY: CDS
<222> LOCATION: (497)..(3655)

<400> SEQUENCE: 3
cagggcacgc tgggtcggcg gagctgaggc tcccagctgt gggcctcgct ggcccggtcg      60
cccagtctcg cgagagttgg gagtaaacag ccccgaatgg agtgcccagg cgtgttcgcc     120
gcggaggcgc cgttatcccg ggcccgccgg ccctgagctc ccggcggcgc agattggctc     180
acagtggttg attgatcaac cccattggac gttggttctg tggtacaaat ggagtacagg     240
actcagtcgt cacggcctga gtgagagaag ccttatttcc aagatggaga agaagcggag     300
aaagaaatga aagcctctct tcaggctgaa ccacaaaagg ccatgggatt taacttttat     360
ttatgttggg caagactgta agatggctga tcagtaatgt tgcagctttt agctgaaaca     420
aaaattcact tttaatcaag aagaaaaaag tgtgatttga atatatgcaa ttttatgatc     480
atattcgctt gtgacc atg aag ctt gtc aac atc tgg ctg ctt ctg ctc gtg    532
                   Met Lys Leu Val Asn Ile Trp Leu Leu Leu Leu Val
                     1               5                  10 gtt ttg ctc tgt ggg aag aaa cat ctg ggc gac aga ctg gaa aag aaa        580
Val Leu Leu Cys Gly Lys Lys His Leu Gly Asp Arg Leu Glu Lys Lys
         15                  20                  25 tct ttt gaa aag gcc cca tgc cct ggc tgt tcc cac ctg act ttg aag        628
Ser Phe Glu Lys Ala Pro Cys Pro Gly Cys Ser His Leu Thr Leu Lys
 30                  35                  40 gtg gaa ttc tca tca aca gtt gtg gaa tat gaa tat att gtg gct ttc        676
Val Glu Phe Ser Ser Thr Val Val Glu Tyr Glu Tyr Ile Val Ala Phe
 45                  50                  55                  60 aat gga tac ttt aca gcc aaa gct aga aat tca ttt att tca agt gcc        724
Asn Gly Tyr Phe Thr Ala Lys Ala Arg Asn Ser Phe Ile Ser Ser Ala
                 65                  70                  75 ctg aag agc agt gaa gta gac aat tgg aga att ata cct cga aac aat        772
Leu Lys Ser Ser Glu Val Asp Asn Trp Arg Ile Ile Pro Arg Asn Asn
             80                  85                  90 cca tcc agt gac tac cct agt gat ttt gag gtg att cag ata aaa gaa        820
Pro Ser Ser Asp Tyr Pro Ser Asp Phe Glu Val Ile Gln Ile Lys Glu
         95                 100                 105 aaa cag aaa gcg ggg ctg cta aca ctt gaa gat cat cca aac atc aaa        868
Lys Gln Lys Ala Gly Leu Leu Thr Leu Glu Asp His Pro Asn Ile Lys
110                 115                 120 cgg gtc acg ccc caa cga aaa gtc ttt cgt tcc ctc aag tat gct gaa        916
Arg Val Thr Pro Gln Arg Lys Val Phe Arg Ser Leu Lys Tyr Ala Glu
125                 130                 135                 140 tct gac ccc aca gta ccc tgc aat gaa acc cgg tgg agc cag aag tgg        964
Ser Asp Pro Thr Val Pro Cys Asn Glu Thr Arg Trp Ser Gln Lys Trp
                145                 150                 155 caa tca tca cgt ccc ctg cga aga gcc agc ctc tcc ctg ggc tct ggc       1012
Gln Ser Ser Arg Pro Leu Arg Arg Ala Ser Leu Ser Leu Gly Ser Gly
            160                 165                 170 ttc tgg cat gct acg gga agg cat tcg agc aga cgg ctg ctg aga gcc       1060
Phe Trp His Ala Thr Gly Arg His Ser Ser Arg Arg Leu Leu Arg Ala
        175                 180                 185 atc ccg cgc cag gtt gcc cag aca ctg cag gca gat gtg ctc tgg cag       1108
Ile Pro Arg Gln Val Ala Gln Thr Leu Gln Ala Asp Val Leu Trp Gln
    190                 195                 200 atg gga tat aca ggt gct aat gta aga gtt gct gtt ttt gac act ggg       1156
Met Gly Tyr Thr Gly Ala Asn Val Arg Val Ala Val Phe Asp Thr Gly
205                 210                 215                 220
```

```
ctg agc gag aag cat ccc cac ttc aaa aat gtg aag gag aga acc aac      1204
Leu Ser Glu Lys His Pro His Phe Lys Asn Val Lys Glu Arg Thr Asn
            225                 230                 235 tgg acc aac gag cga acg ctg gac gat ggg ttg ggc cat ggc aca ttc      1252
Trp Thr Asn Glu Arg Thr Leu Asp Asp Gly Leu Gly His Gly Thr Phe
            240                 245                 250 gtg gca ggt gtg ata gcc agc atg agg gag tgc caa gga ttt gct cca      1300
Val Ala Gly Val Ile Ala Ser Met Arg Glu Cys Gln Gly Phe Ala Pro
            255                 260                 265 gat gca gaa ctt cac att ttc agg gtc ttt acc aat aat cag gta tct      1348
Asp Ala Glu Leu His Ile Phe Arg Val Phe Thr Asn Asn Gln Val Ser
            270                 275                 280 tac aca tct tgg ttt ttg gac gcc ttc aac tat gcc att tta aag aag      1396
Tyr Thr Ser Trp Phe Leu Asp Ala Phe Asn Tyr Ala Ile Leu Lys Lys
285                 290                 295                 300 atc gac gtg tta aac ctc agc atc ggc ggc ccg gac ttc atg gat cat      1444
Ile Asp Val Leu Asn Leu Ser Ile Gly Gly Pro Asp Phe Met Asp His
                305                 310                 315 ccg ttt gtt gac aag gtg tgg gaa tta aca gct aac aat gta atc atg      1492
Pro Phe Val Asp Lys Val Trp Glu Leu Thr Ala Asn Asn Val Ile Met
                320                 325                 330 gtt tct gct att ggc aat gac gga cct ctt tat ggc act ctg aat aac      1540
Val Ser Ala Ile Gly Asn Asp Gly Pro Leu Tyr Gly Thr Leu Asn Asn
                335                 340                 345 cct gct gat caa atg gat gtg att gga gta ggc ggc att gac ttt gaa      1588
Pro Ala Asp Gln Met Asp Val Ile Gly Val Gly Gly Ile Asp Phe Glu
            350                 355                 360 gat aac atc gcc cgc ttt tct tca agg gga atg act acc tgg gag cta      1636
Asp Asn Ile Ala Arg Phe Ser Ser Arg Gly Met Thr Thr Trp Glu Leu
365                 370                 375                 380 cca gga ggc tac ggt cgc atg aaa cct gac att gtc acc tat ggt gct      1684
Pro Gly Gly Tyr Gly Arg Met Lys Pro Asp Ile Val Thr Tyr Gly Ala
                385                 390                 395 ggc gtg cgg ggt tct ggc gtg aaa ggg ggg tgc cgg gcc ctc tca ggg      1732
Gly Val Arg Gly Ser Gly Val Lys Gly Gly Cys Arg Ala Leu Ser Gly
            400                 405                 410 acc agt gtt gct tct cca gtg gtt gca ggt gct gtc acc ttg tta gtg      1780
Thr Ser Val Ala Ser Pro Val Val Ala Gly Ala Val Thr Leu Leu Val
            415                 420                 425 agc aca gtc cag aag cgt gag ctg gtg aat ccc gcc agt atg aag cag      1828
Ser Thr Val Gln Lys Arg Glu Leu Val Asn Pro Ala Ser Met Lys Gln
430                 435                 440 gcc ctg atc gcg tca gcc cgg agg ctc ccc ggg gtc aac atg ttt gag      1876
Ala Leu Ile Ala Ser Ala Arg Arg Leu Pro Gly Val Asn Met Phe Glu
445                 450                 455                 460 caa ggc cac ggc aag ctc gat ctg ctc aga gcc tat cag atc ctc aac      1924
Gln Gly His Gly Lys Leu Asp Leu Leu Arg Ala Tyr Gln Ile Leu Asn
                465                 470                 475 agc tac aag cca cag gca agt ttg agc ccc agc tac ata gat ctg act      1972
Ser Tyr Lys Pro Gln Ala Ser Leu Ser Pro Ser Tyr Ile Asp Leu Thr
            480                 485                 490 gag tgt ccc tac atg tgg ccc tac tgc tcc cag ccc atc tac tat gga      2020
Glu Cys Pro Tyr Met Trp Pro Tyr Cys Ser Gln Pro Ile Tyr Tyr Gly
            495                 500                 505 gga atg ccg aca gtt gtt aat gtc acc atc ctc aac ggc atg gga gtc      2068
Gly Met Pro Thr Val Val Asn Val Thr Ile Leu Asn Gly Met Gly Val
510                 515                 520 aca gga aga att gta gat aag cct gac tgg cag ccc tat ttg cca cag      2116
Thr Gly Arg Ile Val Asp Lys Pro Asp Trp Gln Pro Tyr Leu Pro Gln
```

-continued

| | | |
|---|---|---|
| aac gga gac aac att gaa gtt gcc ttc tcc tac tcc tcg gtc tta tgg<br>Asn Gly Asp Asn Ile Glu Val Ala Phe Ser Tyr Ser Ser Val Leu Trp<br>525                            530                         535                        540<br>                          545                         550                         555 | 2164 |
| cct tgg tcg ggc tac ctg gcc atc tcc att tct gtg acc aag aaa gcg<br>Pro Trp Ser Gly Tyr Leu Ala Ile Ser Ile Ser Val Thr Lys Lys Ala<br>        560                      565                      570 | 2212 |
| gct tcc tgg gaa ggc att gct cag ggc cat gtc atg atc act gtg gct<br>Ala Ser Trp Glu Gly Ile Ala Gln Gly His Val Met Ile Thr Val Ala<br>575                            580                         585 | 2260 |
| tcc cca gca gag aca gag tca aaa aat ggt gca gaa cag act tca aca<br>Ser Pro Ala Glu Thr Glu Ser Lys Asn Gly Ala Glu Gln Thr Ser Thr<br>      590                      595                      600 | 2308 |
| gta aag ctc ccc att aag gtg aag ata att cct act ccc ccg cga agc<br>Val Lys Leu Pro Ile Lys Val Lys Ile Ile Pro Thr Pro Pro Arg Ser<br>605                            610                         615                      620 | 2356 |
| aag aga gtt ctc tgg gat cag tac cac aac ctc cgc tat cca cct ggc<br>Lys Arg Val Leu Trp Asp Gln Tyr His Asn Leu Arg Tyr Pro Pro Gly<br>                        625                      630                        635 | 2404 |
| tat ttc ccc agg gat aat tta agg atg aag aat gac cct tta gac tgg<br>Tyr Phe Pro Arg Asp Asn Leu Arg Met Lys Asn Asp Pro Leu Asp Trp<br>        640                      645                      650 | 2452 |
| aat ggt gat cac atc cac acc aat ttc agg gat atg tac cag cat ctg<br>Asn Gly Asp His Ile His Thr Asn Phe Arg Asp Met Tyr Gln His Leu<br>655                            660                         665 | 2500 |
| aga agc atg ggc tac ttt gta gag gtc ctc ggg gcc ccc ttc acg tgt<br>Arg Ser Met Gly Tyr Phe Val Glu Val Leu Gly Ala Pro Phe Thr Cys<br>      670                      675                      680 | 2548 |
| ttt gat gcc agt cag tat ggc act ttg ctg atg gtg gac agt gag gag<br>Phe Asp Ala Ser Gln Tyr Gly Thr Leu Leu Met Val Asp Ser Glu Glu<br>685                            690                         695                      700 | 2596 |
| gag tac ttc cct gaa gag atc gcc aag ctc cgg agg gac gtg gac aac<br>Glu Tyr Phe Pro Glu Glu Ile Ala Lys Leu Arg Arg Asp Val Asp Asn<br>                        705                      710                      715 | 2644 |
| ggc ctc tcg ctc gtc atc ttc agt gac tgg tac aac act tct gtt atg<br>Gly Leu Ser Leu Val Ile Phe Ser Asp Trp Tyr Asn Thr Ser Val Met<br>                  720                      725                      730 | 2692 |
| aga aaa gtg aag ttt tat gat gaa aac aca agg cag tgg tgg atg ccg<br>Arg Lys Val Lys Phe Tyr Asp Glu Asn Thr Arg Gln Trp Trp Met Pro<br>735                            740                         745 | 2740 |
| gat acc gga gga gct aac atc cca gct ctg aat gag ctg ctg tct gtg<br>Asp Thr Gly Gly Ala Asn Ile Pro Ala Leu Asn Glu Leu Leu Ser Val<br>      750                      755                      760 | 2788 |
| tgg aac atg ggg ttc agc gat ggc ctg tat gaa ggg gag ttc acc ctg<br>Trp Asn Met Gly Phe Ser Asp Gly Leu Tyr Glu Gly Glu Phe Thr Leu<br>765                            770                        775                      780 | 2836 |
| gcc aac cat gac atg tat tat gcg tca ggg tgc agc atc gcg aag ttt<br>Ala Asn His Asp Met Tyr Tyr Ala Ser Gly Cys Ser Ile Ala Lys Phe<br>                  785                      790                      795 | 2884 |
| cca gaa gat ggc gtc gtg ata aca cag act ttc aag gac caa gga ttg<br>Pro Glu Asp Gly Val Val Ile Thr Gln Thr Phe Lys Asp Gln Gly Leu<br>                800                      805                      810 | 2932 |
| gag gtt tta aag cag gaa aca gca gtt gtt gaa aac gtc ccc att ttg<br>Glu Val Leu Lys Gln Glu Thr Ala Val Val Glu Asn Val Pro Ile Leu<br>815                            820                        825 | 2980 |
| gga ctt tat cag att cca gct gag ggt gga ggc cgg att gta ctg tat<br>Gly Leu Tyr Gln Ile Pro Ala Glu Gly Gly Gly Arg Ile Val Leu Tyr<br>      830                      835                      840 | 3028 |
| ggg gac tcc aat tgc ttg gat gac agt cac cga cag aag gac tgc ttt | 3076 |

```
                                                        -continued

Gly Asp Ser Asn Cys Leu Asp Asp Ser His Arg Gln Lys Asp Cys Phe
845                 850                 855                 860 tgg ctt ctg gat gcc ctc ctc cag tac aca tcg tat ggg gtg aca ccg      3124
Trp Leu Leu Asp Ala Leu Leu Gln Tyr Thr Ser Tyr Gly Val Thr Pro
                865                 870                 875 cct agc ctc agt cac tct ggg aac cgc cag cgc cct ccc agt gga gca      3172
Pro Ser Leu Ser His Ser Gly Asn Arg Gln Arg Pro Pro Ser Gly Ala
            880                 885                 890 ggc tca gtc act cca gag agg atg gaa gga aac cat ctt cat cgg tac      3220
Gly Ser Val Thr Pro Glu Arg Met Glu Gly Asn His Leu His Arg Tyr
        895                 900                 905 tcc aag gtt ctg gag gcc cat ttg gga gac cca aaa cct cgg cct cta      3268
Ser Lys Val Leu Glu Ala His Leu Gly Asp Pro Lys Pro Arg Pro Leu
    910                 915                 920 cca gcc tgt cca cgc ttg tct tgg gcc aag cca cag cct tta aac gag      3316
Pro Ala Cys Pro Arg Leu Ser Trp Ala Lys Pro Gln Pro Leu Asn Glu
925                 930                 935                 940 acg gcg ccc agt aac ctt tgg aaa cat cag aag cta ctc tcc att gac      3364
Thr Ala Pro Ser Asn Leu Trp Lys His Gln Lys Leu Leu Ser Ile Asp
                945                 950                 955 ctg gac aag gtg gtg tta ccc aac ttt cga tcg aat cgc cct caa gtg      3412
Leu Asp Lys Val Val Leu Pro Asn Phe Arg Ser Asn Arg Pro Gln Val
            960                 965                 970 agg ccc ttg tcc cct gga gag agc ggc gcc tgg gac att cct gga ggg      3460
Arg Pro Leu Ser Pro Gly Glu Ser Gly Ala Trp Asp Ile Pro Gly Gly
        975                 980                 985 atc atg cct ggc cgc tac aac cag gag gtg ggc cag acc att cct gtc      3508
Ile Met Pro Gly Arg Tyr Asn Gln Glu Val Gly Gln Thr Ile Pro Val
    990                 995                 1000 ttt gcc ttc ctg gga gcc atg gtg gtc ctg gcc ttc ttt gtg gta caa      3556
Phe Ala Phe Leu Gly Ala Met Val Val Leu Ala Phe Phe Val Val Gln
1005                1010                1015                1020 atc aac aag gcc aag agc agg ccg aag cgg agg aag ccc agg gtg aag      3604
Ile Asn Lys Ala Lys Ser Arg Pro Lys Arg Arg Lys Pro Arg Val Lys
                1025                1030                1035 cgc ccg cag ctc atg cag cag gtt cac ccg cca aag acc cct tcg gtg      3652
Arg Pro Gln Leu Met Gln Gln Val His Pro Pro Lys Thr Pro Ser Val
            1040                1045                1050 tga ccggcagcct ggctgaccgt gagggccaga gagagccttc acggacggcg            3705
ctggtgggtg agccgagctg tggtggcggc tggtttaaaa gggatccagt ttccagctgc     3765
aggtttgtta gagtctgttc tacatgggcc tgccctcctg tgatgggcag aggctcctgg     3825
tacatcgaga agattcctgt ggatcccgtc aggagggact tagtggctct gccgccagtg     3885
agacttcccg ccggcagctg tgcgcaccaa agactcggga gaactggaaa ggctgtctgg     3945
ggtcttctga ctgcagggga aggatgtact ttccaaacaa atgatacaac cctgaccaag     4005
ctaaaagacg cttgttaaag gctatttct atatttattg ttgggaaaag tcactttaaa      4065
gacttgtgct atttggaagc aaagctattt tttttgtcag tggaatgcag ttttttttact   4125 attccatcat gaggaacaac atagattcca tgatcttttt aatgacagta cagactgaga    4185
tttgaaggaa acatgcacaa atctgtaaaa catagacctt cgctttattt ttgtaagtat    4245
cacctgccac catgttttgt aatttgaggt cttgatttca ccattgtcgg tgaagaaaat    4305
tttcaataaa tatgtattac ccgtctgaag ctt                                  4338

<210> SEQ ID NO 4
<211> LENGTH: 1052
<212> TYPE: PRT
```

<213> ORGANISM: Homo sapiens

<400> SEQUENCE: 4

```
Met Lys Leu Val Asn Ile Trp Leu Leu Leu Val Leu Leu Cys
 1               5                  10                  15

Gly Lys Lys His Leu Gly Asp Arg Leu Glu Lys Lys Ser Phe Glu Lys
                20                  25                  30

Ala Pro Cys Pro Gly Cys Ser His Leu Thr Leu Lys Val Glu Phe Ser
                35                  40                  45

Ser Thr Val Val Glu Tyr Glu Tyr Ile Val Ala Phe Asn Gly Tyr Phe
        50                  55                  60

Thr Ala Lys Ala Arg Asn Ser Phe Ile Ser Ser Ala Leu Lys Ser Ser
 65                  70                  75                  80

Glu Val Asp Asn Trp Arg Ile Ile Pro Arg Asn Asn Pro Ser Ser Asp
                    85                  90                  95

Tyr Pro Ser Asp Phe Glu Val Ile Gln Ile Lys Glu Lys Gln Lys Ala
                100                 105                 110

Gly Leu Leu Thr Leu Glu Asp His Pro Asn Ile Lys Arg Val Thr Pro
                115                 120                 125

Gln Arg Lys Val Phe Arg Ser Leu Lys Tyr Ala Glu Ser Asp Pro Thr
130                 135                 140

Val Pro Cys Asn Glu Thr Arg Trp Ser Gln Lys Trp Gln Ser Ser Arg
145                 150                 155                 160

Pro Leu Arg Arg Ala Ser Leu Ser Leu Gly Ser Gly Phe Trp His Ala
                165                 170                 175

Thr Gly Arg His Ser Ser Arg Arg Leu Leu Arg Ala Ile Pro Arg Gln
                180                 185                 190

Val Ala Gln Thr Leu Gln Ala Asp Val Leu Trp Gln Met Gly Tyr Thr
                195                 200                 205

Gly Ala Asn Val Arg Val Ala Val Phe Asp Thr Gly Leu Ser Glu Lys
                210                 215                 220

His Pro His Phe Lys Asn Val Lys Glu Arg Thr Asn Trp Thr Asn Glu
225                 230                 235                 240

Arg Thr Leu Asp Asp Gly Leu Gly His Gly Thr Phe Val Ala Gly Val
                245                 250                 255

Ile Ala Ser Met Arg Glu Cys Gln Gly Phe Ala Pro Asp Ala Glu Leu
                260                 265                 270

His Ile Phe Arg Val Phe Thr Asn Asn Gln Val Ser Tyr Thr Ser Trp
                275                 280                 285

Phe Leu Asp Ala Phe Asn Tyr Ala Ile Leu Lys Lys Ile Asp Val Leu
                290                 295                 300

Asn Leu Ser Ile Gly Gly Pro Asp Phe Met Asp His Pro Phe Val Asp
305                 310                 315                 320

Lys Val Trp Glu Leu Thr Ala Asn Asn Val Ile Met Val Ser Ala Ile
                325                 330                 335

Gly Asn Asp Gly Pro Leu Tyr Gly Thr Leu Asn Asn Pro Ala Asp Gln
                340                 345                 350

Met Asp Val Ile Gly Val Gly Gly Ile Asp Phe Glu Asp Asn Ile Ala
                355                 360                 365

Arg Phe Ser Ser Arg Gly Met Thr Thr Trp Glu Leu Pro Gly Gly Tyr
                370                 375                 380

Gly Arg Met Lys Pro Asp Ile Val Thr Tyr Gly Ala Gly Val Arg Gly
385                 390                 395                 400
```

-continued

```
Ser Gly Val Lys Gly Gly Cys Arg Ala Leu Ser Gly Thr Ser Val Ala
            405                 410                 415
Ser Pro Val Val Ala Gly Ala Val Thr Leu Leu Val Ser Thr Val Gln
            420                 425                 430
Lys Arg Glu Leu Val Asn Pro Ala Ser Met Lys Gln Ala Leu Ile Ala
            435                 440                 445
Ser Ala Arg Arg Leu Pro Gly Val Asn Met Phe Glu Gln Gly His Gly
450                 455                 460
Lys Leu Asp Leu Leu Arg Ala Tyr Gln Ile Leu Asn Ser Tyr Lys Pro
465                 470                 475                 480
Gln Ala Ser Leu Ser Pro Ser Tyr Ile Asp Leu Thr Glu Cys Pro Tyr
            485                 490                 495
Met Trp Pro Tyr Cys Ser Gln Pro Ile Tyr Tyr Gly Gly Met Pro Thr
            500                 505                 510
Val Val Asn Val Thr Ile Leu Asn Gly Met Gly Val Thr Gly Arg Ile
            515                 520                 525
Val Asp Lys Pro Asp Trp Gln Pro Tyr Leu Pro Gln Asn Gly Asp Asn
            530                 535                 540
Ile Glu Val Ala Phe Ser Tyr Ser Ser Val Leu Trp Pro Trp Ser Gly
545                 550                 555                 560
Tyr Leu Ala Ile Ser Ile Ser Val Thr Lys Lys Ala Ala Ser Trp Glu
            565                 570                 575
Gly Ile Ala Gln Gly His Val Met Ile Thr Val Ala Ser Pro Ala Glu
            580                 585                 590
Thr Glu Ser Lys Asn Gly Ala Glu Gln Thr Ser Thr Val Lys Leu Pro
            595                 600                 605
Ile Lys Val Lys Ile Ile Pro Thr Pro Arg Ser Lys Arg Val Leu
            610                 615                 620
Trp Asp Gln Tyr His Asn Leu Arg Tyr Pro Pro Gly Tyr Phe Pro Arg
625                 630                 635                 640
Asp Asn Leu Arg Met Lys Asn Asp Pro Leu Asp Trp Asn Gly Asp His
            645                 650                 655
Ile His Thr Asn Phe Arg Asp Met Tyr Gln His Leu Arg Ser Met Gly
            660                 665                 670
Tyr Phe Val Glu Val Leu Gly Ala Pro Phe Thr Cys Phe Asp Ala Ser
            675                 680                 685
Gln Tyr Gly Thr Leu Leu Met Val Asp Ser Glu Glu Tyr Phe Pro
            690                 695                 700
Glu Glu Ile Ala Lys Leu Arg Arg Asp Val Asp Asn Gly Leu Ser Leu
705                 710                 715                 720
Val Ile Phe Ser Asp Trp Tyr Asn Thr Ser Val Met Arg Lys Val Lys
            725                 730                 735
Phe Tyr Asp Glu Asn Thr Arg Gln Trp Trp Met Pro Thr Gly Gly
            740                 745                 750
Ala Asn Ile Pro Ala Leu Asn Glu Leu Leu Ser Val Trp Asn Met Gly
            755                 760                 765
Phe Ser Asp Gly Leu Tyr Glu Gly Glu Phe Thr Leu Ala Asn His Asp
            770                 775                 780
Met Tyr Tyr Ala Ser Gly Cys Ser Ile Ala Lys Phe Pro Glu Asp Gly
785                 790                 795                 800
Val Val Ile Thr Gln Thr Phe Lys Asp Gln Gly Leu Glu Val Leu Lys
            805                 810                 815
Gln Glu Thr Ala Val Val Glu Asn Val Pro Ile Leu Gly Leu Tyr Gln
```

-continued

```
                       820                 825                 830
Ile Pro Ala Glu Gly Gly Gly Arg Ile Val Leu Tyr Gly Asp Ser Asn
        835                 840                 845

Cys Leu Asp Asp Ser His Arg Gln Lys Asp Cys Phe Trp Leu Leu Asp
    850                 855                 860

Ala Leu Leu Gln Tyr Thr Ser Tyr Gly Val Thr Pro Pro Ser Leu Ser
865                 870                 875                 880

His Ser Gly Asn Arg Gln Arg Pro Pro Ser Gly Ala Gly Ser Val Thr
                885                 890                 895

Pro Glu Arg Met Glu Gly Asn His Leu His Arg Tyr Ser Lys Val Leu
            900                 905                 910

Glu Ala His Leu Gly Asp Pro Lys Pro Arg Pro Leu Pro Ala Cys Pro
        915                 920                 925

Arg Leu Ser Trp Ala Lys Pro Gln Pro Leu Asn Glu Thr Ala Pro Ser
    930                 935                 940

Asn Leu Trp Lys His Gln Lys Leu Leu Ser Ile Asp Leu Asp Lys Val
945                 950                 955                 960

Val Leu Pro Asn Phe Arg Ser Asn Arg Pro Gln Val Arg Pro Leu Ser
                965                 970                 975

Pro Gly Glu Ser Gly Ala Trp Asp Ile Pro Gly Gly Ile Met Pro Gly
            980                 985                 990

Arg Tyr Asn Gln Glu Val Gly Gln Thr Ile Pro Val Phe Ala Phe Leu
        995                 1000                1005

Gly Ala Met Val Val Leu Ala Phe Phe Val Val Gln Ile Asn Lys Ala
    1010                1015                1020

Lys Ser Arg Pro Lys Arg Arg Lys Pro Arg Val Lys Arg Pro Gln Leu
1025                1030                1035                1040

Met Gln Gln Val His Pro Pro Lys Thr Pro Ser Val
                1045                1050

<210> SEQ ID NO 5
<211> LENGTH: 4198
<212> TYPE: DNA
<213> ORGANISM: Cricetulus griseus
<220> FEATURE:
<221> NAME/KEY: CDS
<222> LOCATION: (387)..(3545)

<400> SEQUENCE: 5
tgttcgcggc agaggcgccg ttcccccggg cccgccgacc tcgagcctga ggcggacgca      60
ggtcggccct cagagtggtt tcttgggcat ccccactaga tttgggtctg tggtgcaaat     120
ggagtctagg actcagtcga ctctgcccta atgagagaag cccctgtcca agatggagaa     180
gaagcggaga aagaaatgaa agcctctttt tgggccaagc tgtgggtgac catgggactg     240
aggttttctt tacgttggac aagtctgtag gatggctgat cagtaaggtt gcagctttta     300
gccaaaacag aaattcactt ctgatcaagg aagaacctag tgcgatttga atttatgcaa     360
ttttatgacc atattcactt aggacc atg aag ctc atc aac atc tgg ctt ctt     413
                              Met Lys Leu Ile Asn Ile Trp Leu Leu
                                1               5 ctg ctg gtg gtt ttg ctc tgt gga aag aag cat ctg ggt gac agg ctg     461
Leu Leu Val Val Leu Leu Cys Gly Lys Lys His Leu Gly Asp Arg Leu
 10              15                  20                  25 ggg aag aaa gcg ttt gaa aag gca tca tgc cct agc tgt tcc cac ctg     509
Gly Lys Lys Ala Phe Glu Lys Ala Ser Cys Pro Ser Cys Ser His Leu
                30                  35                  40 act ttg aag gtg gaa ttc tcc tca act gtg gtg gaa tat gaa tat att     557
```

-continued

```
Thr Leu Lys Val Glu Phe Ser Ser Thr Val Val Glu Tyr Glu Tyr Ile
             45                  50                  55 gtg gct ttc aac gga tac ttc aca gcc aaa gct aga aac tca ttt att        605
Val Ala Phe Asn Gly Tyr Phe Thr Ala Lys Ala Arg Asn Ser Phe Ile
         60                  65                  70 tca agt gct ctg aaa agc agt gaa gta gac aac tgg aga att ata cct        653
Ser Ser Ala Leu Lys Ser Ser Glu Val Asp Asn Trp Arg Ile Ile Pro
     75                  80                  85 cgg aac aac cca tcc agt gac tac cct agt gat ttt gag gtg att cag        701
Arg Asn Asn Pro Ser Ser Asp Tyr Pro Ser Asp Phe Glu Val Ile Gln
 90                  95                 100                 105 ata aaa gag aag cag aag gcc ggg ctg ctc aca ctt gaa gat cat cca        749
Ile Lys Glu Lys Gln Lys Ala Gly Leu Leu Thr Leu Glu Asp His Pro
             110                 115                 120 aac atc aag cgg gtg aca cct caa cgc aaa gtc ttt cgt tcc ttg aag        797
Asn Ile Lys Arg Val Thr Pro Gln Arg Lys Val Phe Arg Ser Leu Lys
         125                 130                 135 ttt gct gaa tct gac ccc att gtg cca tgt aat gaa act cgg tgg agc        845
Phe Ala Glu Ser Asp Pro Ile Val Pro Cys Asn Glu Thr Arg Trp Ser
     140                 145                 150 cag aag tgg cag tca tca cga ccc ctg aga aga gcc agt ctc tcc ctg        893
Gln Lys Trp Gln Ser Ser Arg Pro Leu Arg Arg Ala Ser Leu Ser Leu
 155                 160                 165 ggc tct gga ttc tgg cat gca aca gga aga cat tca agc cgg cga ttg        941
Gly Ser Gly Phe Trp His Ala Thr Gly Arg His Ser Ser Arg Arg Leu
170                 175                 180                 185 ctg aga gcc att cct cga cag gtt gcc cag aca ttg cag gca gat gtg        989
Leu Arg Ala Ile Pro Arg Gln Val Ala Gln Thr Leu Gln Ala Asp Val
             190                 195                 200 ctg tgg cag atg gga tac aca ggt gct aat gtc agg gtt gct gtt ttt       1037
Leu Trp Gln Met Gly Tyr Thr Gly Ala Asn Val Arg Val Ala Val Phe
         205                 210                 215 gat act ggg ctc agt gag aag cat cca cac ttc aag aat gtg aag gag       1085
Asp Thr Gly Leu Ser Glu Lys His Pro His Phe Lys Asn Val Lys Glu
     220                 225                 230 aga acc aac tgg acc aat gag cgg acc ctg gat gat ggg ctg ggc cat       1133
Arg Thr Asn Trp Thr Asn Glu Arg Thr Leu Asp Asp Gly Leu Gly His
 235                 240                 245 ggc aca ttt gtc gca ggt gtg att gcc agc atg agg gag tgc cag gga       1181
Gly Thr Phe Val Ala Gly Val Ile Ala Ser Met Arg Glu Cys Gln Gly
250                 255                 260                 265 ttt gcc cca gat gca gag ctg cac atc ttc cgg gtc ttt acc aac aat       1229
Phe Ala Pro Asp Ala Glu Leu His Ile Phe Arg Val Phe Thr Asn Asn
             270                 275                 280 cag gtg tct tac aca tct tgg ttt ttg gac gct ttc aac tat gcc atc       1277
Gln Val Ser Tyr Thr Ser Trp Phe Leu Asp Ala Phe Asn Tyr Ala Ile
         285                 290                 295 cta aag aag att gat gtt cta aac ctt agc atc ggc ggg cct gac ttc       1325
Leu Lys Lys Ile Asp Val Leu Asn Leu Ser Ile Gly Gly Pro Asp Phe
     300                 305                 310 atg gat cat ccc ttt gtt gac aag gtg tgg gaa tta aca gct aac aat       1373
Met Asp His Pro Phe Val Asp Lys Val Trp Glu Leu Thr Ala Asn Asn
 315                 320                 325 gta atc atg gtt tct gct atc ggc aat gat gga cct ctt tat ggc act       1421
Val Ile Met Val Ser Ala Ile Gly Asn Asp Gly Pro Leu Tyr Gly Thr
330                 335                 340                 345 ctg aat aac cca gct gat cag atg gat gtg att gga gtg ggt ggc att       1469
Leu Asn Asn Pro Ala Asp Gln Met Asp Val Ile Gly Val Gly Gly Ile
             350                 355                 360
```

```
gac ttt gaa gat aac atc gcc cgc ttt tct tcc agg gga atg act acc    1517
Asp Phe Glu Asp Asn Ile Ala Arg Phe Ser Ser Arg Gly Met Thr Thr
            365                 370                 375 tgg gaa cta cca gga ggc tat ggt cgc gtg aaa cct gac att gtc acc    1565
Trp Glu Leu Pro Gly Gly Tyr Gly Arg Val Lys Pro Asp Ile Val Thr
        380                 385                 390 tat ggt gcc gga gtg cgg ggt tcc ggt gtg aaa ggg ggc tgc cgg gca    1613
Tyr Gly Ala Gly Val Arg Gly Ser Gly Val Lys Gly Gly Cys Arg Ala
    395                 400                 405 ctc tca ggg acc agt gtc gct tcc cca gtg gtt gct ggg gct gtc acc    1661
Leu Ser Gly Thr Ser Val Ala Ser Pro Val Val Ala Gly Ala Val Thr
410                 415                 420                 425 ttg tta gta agc aca gtg cag aag cgg gag cta gtg aat cct gcc agt    1709
Leu Leu Val Ser Thr Val Gln Lys Arg Glu Leu Val Asn Pro Ala Ser
                430                 435                 440 gtg aag caa gcc ctg att gca tca gcc cgg agg ctt cct ggt gtt aac    1757
Val Lys Gln Ala Leu Ile Ala Ser Ala Arg Arg Leu Pro Gly Val Asn
            445                 450                 455 atg ttc gag caa ggc cat ggc aag ctg gat ctg ctg cga gcc tat cag    1805
Met Phe Glu Gln Gly His Gly Lys Leu Asp Leu Leu Arg Ala Tyr Gln
        460                 465                 470 atc ctc agc agc tac aaa cca cag gcg agc ttg agt cct agc tac atc    1853
Ile Leu Ser Ser Tyr Lys Pro Gln Ala Ser Leu Ser Pro Ser Tyr Ile
    475                 480                 485 gac ctg act gag tgt ccc tac atg tgg cct tac tgt tct cag ccc atc    1901
Asp Leu Thr Glu Cys Pro Tyr Met Trp Pro Tyr Cys Ser Gln Pro Ile
490                 495                 500                 505 tac tat gga gga atg cca aca att gtt aat gtc acc atc ctc aat ggc    1949
Tyr Tyr Gly Gly Met Pro Thr Ile Val Asn Val Thr Ile Leu Asn Gly
                510                 515                 520 atg gga gtc aca gga aga att gtg gat aag cct gag tgg cgg ccc tat    1997
Met Gly Val Thr Gly Arg Ile Val Asp Lys Pro Glu Trp Arg Pro Tyr
            525                 530                 535 tta cca cag aat gga gac aac att gaa gtg gcc ttc tcc tac tcc tca    2045
Leu Pro Gln Asn Gly Asp Asn Ile Glu Val Ala Phe Ser Tyr Ser Ser
        540                 545                 550 gtg tta tgg cct tgg tca ggc tac ctg gcc atc tcc att tct gtg acc    2093
Val Leu Trp Pro Trp Ser Gly Tyr Leu Ala Ile Ser Ile Ser Val Thr
    555                 560                 565 aag aag gca gct tcc tgg gaa ggc att gca cag ggt cac atc atg atc    2141
Lys Lys Ala Ala Ser Trp Glu Gly Ile Ala Gln Gly His Ile Met Ile
570                 575                 580                 585 acg gtg gct tcc cca gca gag acg gaa gca aaa aat ggt gcc gag cat    2189
Thr Val Ala Ser Pro Ala Glu Thr Glu Ala Lys Asn Gly Ala Glu His
                590                 595                 600 act tcc aca gtg aag ctt ccc att aag gtg aag atc att ccc acc cct    2237
Thr Ser Thr Val Lys Leu Pro Ile Lys Val Lys Ile Ile Pro Thr Pro
            605                 610                 615 cct cgg agc aag aga gtc ctc tgg gac cag tat cac aac ctc cgc tac    2285
Pro Arg Ser Lys Arg Val Leu Trp Asp Gln Tyr His Asn Leu Arg Tyr
        620                 625                 630 ccc cca ggc tac ttt ccc agg gac aac ttg cgg atg aag aat gat cct    2333
Pro Pro Gly Tyr Phe Pro Arg Asp Asn Leu Arg Met Lys Asn Asp Pro
    635                 640                 645 tta gac tgg aat ggc gac cat gtc cac acc aat ttc agg gac atg tac    2381
Leu Asp Trp Asn Gly Asp His Val His Thr Asn Phe Arg Asp Met Tyr
650                 655                 660                 665 cag cac ctg cgc agc atg ggc tac ttc gtg gag gtg ctc ggt gcc cca    2429
Gln His Leu Arg Ser Met Gly Tyr Phe Val Glu Val Leu Gly Ala Pro
                670                 675                 680
```

-continued

| | | |
|---|---|---|
| ttc acg tgc ttt gat gct aca cag tat ggc act ttg ctc atg gtg gat<br>Phe Thr Cys Phe Asp Ala Thr Gln Tyr Gly Thr Leu Leu Met Val Asp<br>                  685                          690                      695 | 2477 |
| agt gaa gaa gag tac ttc cca gag gag att gcc aag ctg agg agg gac<br>Ser Glu Glu Glu Tyr Phe Pro Glu Glu Ile Ala Lys Leu Arg Arg Asp<br>        700                        705                      710 | 2525 |
| gtg gac aat ggc ctt tcc ctc gtc atc ttc agt gac tgg tac aac act<br>Val Asp Asn Gly Leu Ser Leu Val Ile Phe Ser Asp Trp Tyr Asn Thr<br>715                            720                      725 | 2573 |
| tct gtt atg aga aaa gtg aag ttt tac gat gaa aac aca agg cag tgg<br>Ser Val Met Arg Lys Val Lys Phe Tyr Asp Glu Asn Thr Arg Gln Trp<br>730                         735                      740                      745 | 2621 |
| tgg atg cca gat act gga gga gcc aac atc cca gct ctg aac gag ctg<br>Trp Met Pro Asp Thr Gly Gly Ala Asn Ile Pro Ala Leu Asn Glu Leu<br>                  750                          755                      760 | 2669 |
| ctg tct gtg tgg aac atg ggg ttc agc gat ggc ctt tat gaa ggg gag<br>Leu Ser Val Trp Asn Met Gly Phe Ser Asp Gly Leu Tyr Glu Gly Glu<br>                      765                          770                      775 | 2717 |
| ttt gcc ctg gcg aat cat gac atg tat tat gca tcg gga tgc agc atc<br>Phe Ala Leu Ala Asn His Asp Met Tyr Tyr Ala Ser Gly Cys Ser Ile<br>                  780                          785                      790 | 2765 |
| gcc aag ttt cca gaa gat ggt gtt gtg atc aca cag act ttc aag gac<br>Ala Lys Phe Pro Glu Asp Gly Val Val Ile Thr Gln Thr Phe Lys Asp<br>795                            800                      805 | 2813 |
| caa gga ttg gag gtc tta aaa caa gag aca gca gtt gtt gaa aat gtt<br>Gln Gly Leu Glu Val Leu Lys Gln Glu Thr Ala Val Val Glu Asn Val<br>810                         815                      820                      825 | 2861 |
| ccc att ttg ggg ctt tat cag att cca gct gaa ggt ggg ggc cgg atc<br>Pro Ile Leu Gly Leu Tyr Gln Ile Pro Ala Glu Gly Gly Gly Arg Ile<br>                  830                          835                      840 | 2909 |
| gtg ttg tat gga gat tcc aat tgc ttg gat gac agt cac aga cag aag<br>Val Leu Tyr Gly Asp Ser Asn Cys Leu Asp Asp Ser His Arg Gln Lys<br>                      845                          850                      855 | 2957 |
| gat tgc ttt tgg ctt ctg gat gca ctc ctt cag tac aca tca tat ggc<br>Asp Cys Phe Trp Leu Leu Asp Ala Leu Leu Gln Tyr Thr Ser Tyr Gly<br>                  860                          865                      870 | 3005 |
| gtg aac cct ccc agc ctc agc cat tca ggg aac cgg cag cgc cca ccc<br>Val Asn Pro Pro Ser Leu Ser His Ser Gly Asn Arg Gln Arg Pro Pro<br>875                            880                      885 | 3053 |
| agt gga gct ggc ttg gcc cct cct gaa agg atg gaa gga aac cac ctt<br>Ser Gly Ala Gly Leu Ala Pro Pro Glu Arg Met Glu Gly Asn His Leu<br>890                         895                      900                      905 | 3101 |
| cat cga tac tcc aag gtt ctt gag gcc cat ctg gga gac cca aaa cct<br>His Arg Tyr Ser Lys Val Leu Glu Ala His Leu Gly Asp Pro Lys Pro<br>                  910                          915                      920 | 3149 |
| cgg cct ctt cca gcc tgt cca cac ttg tca tgg gcc aag cca cag cct<br>Arg Pro Leu Pro Ala Cys Pro His Leu Ser Trp Ala Lys Pro Gln Pro<br>                  925                          930                      935 | 3197 |
| ttg aat gag act gcg ccc agt aat ctt tgg aaa cat cag aag ctg ctc<br>Leu Asn Glu Thr Ala Pro Ser Asn Leu Trp Lys His Gln Lys Leu Leu<br>                  940                          945                      950 | 3245 |
| tcc att gac ctg gac aaa gta gtg tta ccc aac ttt cga tcg aat cgc<br>Ser Ile Asp Leu Asp Lys Val Val Leu Pro Asn Phe Arg Ser Asn Arg<br>955                            960                      965 | 3293 |
| cct caa gtg aga cct ttg tcc cct gga gaa agt ggt gcc tgg gac att<br>Pro Gln Val Arg Pro Leu Ser Pro Gly Glu Ser Gly Ala Trp Asp Ile<br>970                         975                      980                      985 | 3341 |
| cct gga ggg atc atg cct ggc cgc tac aac caa gag gtg ggc cag acc<br>Pro Gly Gly Ile Met Pro Gly Arg Tyr Asn Gln Glu Val Gly Gln Thr | 3389 |

-continued

```
                   990             995            1000
atc cct gtc ttt gcc ttc ctc gga gcc atg gtg gcc ctg gcc ttc ttt      3437
Ile Pro Val Phe Ala Phe Leu Gly Ala Met Val Ala Leu Ala Phe Phe
        1005            1010           1015 gtg gta cag atc agc aag gcc aaa agc cgg ccg aag cgg agg agg ccc      3485
Val Val Gln Ile Ser Lys Ala Lys Ser Arg Pro Lys Arg Arg Arg Pro
        1020            1025           1030 agg gca aag cgt cca cag ctt aca cag cag acc cac cca agg acc          3533
Arg Ala Lys Arg Pro Gln Leu Thr Gln Gln Thr His Pro Arg Thr
    1035            1040            1045 ccg tca gtg tga tcatcacagt ggccagccac agaagccaac aagccttgga          3585
Pro Ser Val
1050 ccactctgat ggccacacag ggcatcagaa gagcatcctg ggaggtgcct atttccaagg    3645
gaccccatct ccagcttgtg gctgggttag tgtgttctcc ccaggcatct ctgagttaca    3705
tcctgaagta cctcactgtg ctgggctctt gacaggaggt gctcagtagc tcagcctcca    3765
gtggtgtcag caggcccagt gacagtgcac caaagacaca gagcctggaa gggctgtcgg    3825
gacacacttt ctacataaag cttacaatcc tgaccaagcg aagaaatgct tgttacaggc    3885
tattttctat atttattgtg gggagagtca ctttaaagac ttgtactgtt tggaagcaaa    3945
gctgttgtgt ttgtcagttg agtgcagttt tctgcagtga catcataagg agtcagatcc    4005
catgaccttt tgatgagag acagactga actgaaggc atgtgcacag atctgggaaa       4065
tgcaagcctt cgctttattt ttataagtat caactgccat catgttttgt aatttggggt    4125
cttgatttca ccattgttgg tgaaagaaat tttcaataaa tatgcataac cttaaaaaaa    4185
aaaaaaaaaa aaa                                                       4198
```

<210> SEQ ID NO 6
<211> LENGTH: 1052
<212> TYPE: PRT
<213> ORGANISM: Cricetulus griseus

<400> SEQUENCE: 6

```
Met Lys Leu Ile Asn Ile Trp Leu Leu Leu Leu Val Val Leu Leu Cys
  1               5                  10                  15

Gly Lys Lys His Leu Gly Asp Arg Leu Gly Lys Lys Ala Phe Glu Lys
             20                  25                  30

Ala Ser Cys Pro Ser Cys Ser His Leu Thr Leu Lys Val Glu Phe Ser
         35                  40                  45

Ser Thr Val Val Glu Tyr Glu Tyr Ile Val Ala Phe Asn Gly Tyr Phe
     50                  55                  60

Thr Ala Lys Ala Arg Asn Ser Phe Ile Ser Ser Ala Leu Lys Ser Ser
 65                  70                  75                  80

Glu Val Asp Asn Trp Arg Ile Ile Pro Arg Asn Asn Pro Ser Ser Asp
                 85                  90                  95

Tyr Pro Ser Asp Phe Glu Val Ile Gln Ile Lys Glu Lys Gln Lys Ala
            100                 105                 110

Gly Leu Leu Thr Leu Glu Asp His Pro Asn Ile Lys Arg Val Thr Pro
        115                 120                 125

Gln Arg Lys Val Phe Arg Ser Leu Lys Phe Ala Glu Ser Asp Pro Ile
    130                 135                 140

Val Pro Cys Asn Glu Thr Arg Trp Ser Gln Lys Trp Gln Ser Ser Arg
145                 150                 155                 160

Pro Leu Arg Arg Ala Ser Leu Ser Leu Gly Ser Gly Phe Trp His Ala
```

-continued

```
                  165                 170                 175
Thr Gly Arg His Ser Arg Arg Leu Leu Arg Ala Ile Pro Arg Gln
                180                 185                 190
Val Ala Gln Thr Leu Gln Ala Asp Val Leu Trp Gln Met Gly Tyr Thr
                195                 200                 205
Gly Ala Asn Val Arg Val Ala Val Phe Asp Thr Gly Leu Ser Glu Lys
                210                 215                 220
His Pro His Phe Lys Asn Val Lys Glu Arg Thr Asn Trp Thr Asn Glu
225                 230                 235                 240
Arg Thr Leu Asp Asp Gly Leu Gly His Gly Thr Phe Val Ala Gly Val
                245                 250                 255
Ile Ala Ser Met Arg Glu Cys Gln Gly Phe Ala Pro Asp Ala Glu Leu
                260                 265                 270
His Ile Phe Arg Val Phe Thr Asn Asn Gln Val Ser Tyr Thr Ser Trp
                275                 280                 285
Phe Leu Asp Ala Phe Asn Tyr Ala Ile Leu Lys Lys Ile Asp Val Leu
                290                 295                 300
Asn Leu Ser Ile Gly Gly Pro Asp Phe Met Asp His Pro Phe Val Asp
305                 310                 315                 320
Lys Val Trp Glu Leu Thr Ala Asn Asn Val Ile Met Val Ser Ala Ile
                325                 330                 335
Gly Asn Asp Gly Pro Leu Tyr Gly Thr Leu Asn Asn Pro Ala Asp Gln
                340                 345                 350
Met Asp Val Ile Gly Val Gly Gly Ile Asp Phe Glu Asp Asn Ile Ala
                355                 360                 365
Arg Phe Ser Ser Arg Gly Met Thr Thr Trp Glu Leu Pro Gly Gly Tyr
                370                 375                 380
Gly Arg Val Lys Pro Asp Ile Val Thr Tyr Gly Ala Gly Val Arg Gly
385                 390                 395                 400
Ser Gly Val Lys Gly Gly Cys Arg Ala Leu Ser Gly Thr Ser Val Ala
                405                 410                 415
Ser Pro Val Val Ala Gly Ala Val Thr Leu Leu Val Ser Thr Val Gln
                420                 425                 430
Lys Arg Glu Leu Val Asn Pro Ala Ser Val Lys Gln Ala Leu Ile Ala
                435                 440                 445
Ser Ala Arg Arg Leu Pro Gly Val Asn Met Phe Glu Gln Gly His Gly
                450                 455                 460
Lys Leu Asp Leu Leu Arg Ala Tyr Gln Ile Leu Ser Ser Tyr Lys Pro
465                 470                 475                 480
Gln Ala Ser Leu Ser Pro Ser Tyr Ile Asp Leu Thr Glu Cys Pro Tyr
                485                 490                 495
Met Trp Pro Tyr Cys Ser Gln Pro Ile Tyr Tyr Gly Gly Met Pro Thr
                500                 505                 510
Ile Val Asn Val Thr Ile Leu Asn Gly Met Gly Val Thr Gly Arg Ile
                515                 520                 525
Val Asp Lys Pro Glu Trp Arg Pro Tyr Leu Pro Gln Asn Gly Asp Asn
                530                 535                 540
Ile Glu Val Ala Phe Ser Tyr Ser Ser Val Leu Trp Pro Trp Ser Gly
545                 550                 555                 560
Tyr Leu Ala Ile Ser Ile Ser Val Thr Lys Lys Ala Ala Ser Trp Glu
                565                 570                 575
Gly Ile Ala Gln Gly His Ile Met Ile Thr Val Ala Ser Pro Ala Glu
                580                 585                 590
```

```
Thr Glu Ala Lys Asn Gly Ala Glu His Thr Ser Thr Val Lys Leu Pro
            595                 600                 605

Ile Lys Val Lys Ile Ile Pro Thr Pro Pro Arg Ser Lys Arg Val Leu
610                 615                 620

Trp Asp Gln Tyr His Asn Leu Arg Tyr Pro Pro Gly Tyr Phe Pro Arg
625                 630                 635                 640

Asp Asn Leu Arg Met Lys Asn Asp Pro Leu Asp Trp Asn Gly Asp His
                645                 650                 655

Val His Thr Asn Phe Arg Asp Met Tyr Gln His Leu Arg Ser Met Gly
            660                 665                 670

Tyr Phe Val Glu Val Leu Gly Ala Pro Phe Thr Cys Phe Asp Ala Thr
        675                 680                 685

Gln Tyr Gly Thr Leu Leu Met Val Asp Ser Glu Glu Tyr Phe Pro
    690                 695                 700

Glu Glu Ile Ala Lys Leu Arg Arg Asp Val Asp Asn Gly Leu Ser Leu
705                 710                 715                 720

Val Ile Phe Ser Asp Trp Tyr Asn Thr Ser Val Met Arg Lys Val Lys
                725                 730                 735

Phe Tyr Asp Glu Asn Thr Arg Gln Trp Trp Met Pro Asp Thr Gly Gly
                740                 745                 750

Ala Asn Ile Pro Ala Leu Asn Glu Leu Leu Ser Val Trp Asn Met Gly
            755                 760                 765

Phe Ser Asp Gly Leu Tyr Glu Gly Glu Phe Ala Leu Ala Asn His Asp
        770                 775                 780

Met Tyr Tyr Ala Ser Gly Cys Ser Ile Ala Lys Phe Pro Glu Asp Gly
785                 790                 795                 800

Val Val Ile Thr Gln Thr Phe Lys Asp Gln Gly Leu Glu Val Leu Lys
                805                 810                 815

Gln Glu Thr Ala Val Val Glu Asn Val Pro Ile Leu Gly Leu Tyr Gln
            820                 825                 830

Ile Pro Ala Glu Gly Gly Gly Arg Ile Val Leu Tyr Gly Asp Ser Asn
        835                 840                 845

Cys Leu Asp Asp Ser His Arg Gln Lys Asp Cys Phe Trp Leu Leu Asp
850                 855                 860

Ala Leu Leu Gln Tyr Thr Ser Tyr Gly Val Asn Pro Pro Ser Leu Ser
865                 870                 875                 880

His Ser Gly Asn Arg Gln Arg Pro Pro Ser Gly Ala Gly Leu Ala Pro
                885                 890                 895

Pro Glu Arg Met Glu Gly Asn His Leu His Arg Tyr Ser Lys Val Leu
            900                 905                 910

Glu Ala His Leu Gly Asp Pro Lys Pro Arg Pro Leu Pro Ala Cys Pro
        915                 920                 925

His Leu Ser Trp Ala Lys Pro Gln Pro Leu Asn Glu Thr Ala Pro Ser
    930                 935                 940

Asn Leu Trp Lys His Gln Lys Leu Leu Ser Ile Asp Leu Asp Lys Val
945                 950                 955                 960

Val Leu Pro Asn Phe Arg Ser Asn Arg Pro Gln Val Arg Pro Leu Ser
                965                 970                 975

Pro Gly Glu Ser Gly Ala Trp Asp Ile Pro Gly Gly Ile Met Pro Gly
            980                 985                 990

Arg Tyr Asn Gln Glu Val Gly Gln Thr Ile Pro Val Phe Ala Phe Leu
        995                 1000                1005
```

```
-continued

Gly Ala Met Val Ala Leu Ala Phe Phe Val Val Gln Ile Ser Lys Ala
    1010            1015            1020

Lys Ser Arg Pro Lys Arg Arg Pro Arg Ala Lys Arg Pro Gln Leu
1025            1030            1035            1040

Thr Gln Gln Thr His Pro Pro Arg Thr Pro Ser Val
                1045            1050
```

PROMOTER SEQUENCES

CROSS REFERENCE TO RELATED APPLICATIONS

This application claims priority from Swedish Patent Application No. 0002417-4, filed Jun. 27, 2000, and U.S. Provisional Patent Application Serial No. 60/216,414, filed Jul. 6, 2000. These applications are incorporated herein by reference in their entirety.

TECHNICAL FIELD

The present invention relates an isolated human Site-1 Protease promoter region. The invention also relates to screening methods for agents decreasing the expression of Site-1 protease and thereby being potentially useful for the treatment of medical conditions related to obesity and/or diabetes.

BACKGROUND ART

Sterol Regulatory Element-Binding Proteins (SREBPs)

The integrity of cell membranes is maintained by a balance between the amount of cholesterol and the amounts of unsaturated and saturated fatty acids in phospholipids. This balance is partly maintained by membrane-bound transcription factors called Sterol Regulatory Element-Binding Proteins (SREBPs; for reviews, see Brown & Goldstein (1997) Cell 89, 331–340; Brown & Goldstein (1999) Proc. Natl. Acad. Sci. U.S.A. 96, 11041–11048) that activate genes encoding enzymes of cholesterol and fatty acid biosynthesis. To enhance transcription, the active $NH_2$-terminal domains of SREBPs are released from endoplasmic reticulum membranes by two sequential cleavages. The first is catalyzed by Site-1 protease (S1P), a membrane-bound subtilisin-related serine protease that cleaves the hydrophilic loop of SREBP that projects into the endoplasmic reticulum lumen. The second cleavage, at Site-2, requires the action of S2P, a hydrophobic protein that appears to be a zinc metalloprotease. These regulated proteolytic cleavage reactions are ultimately responsible for controlling the level of cholesterol in membranes, cells, and blood.

Three isoforms of SREBPs have been identified. SREBP-1a and SREBP-1c are encoded by a single gene and differ in their N-terminal acid transcription activation domains. The N-terminus of SREBP-1a is longer and includes additional acidic amino acids, consistent with the observation that it is a more powerful transcription factor (Pai et al. (1998) Proc. Natl. Acad. Sci. U.S.A. 40, 26138–26148). SREBP-2 is produced by a different gene and contains a long activation domain resembling that of SREBP-1a. Recent evidence suggests that the main function of SREBP-2 is to regulate cholesterol synthesis whilst that of SREBP-1 is to regulate fatty acid synthesis (Pai et al., supra).

Inhibition of SREBP transcription factor function will lead to reduced cellular synthesis of free fatty acids and cholesterol, the clinical benefits of which are expected to include increased cellular insulin sensitivity and reduced coronary artery disease (CAD). Furthermore, SREBP-1 represents a cellular mechanism for increasing both fat cell size and number (Kim et al. (1998) J. Clin. Invest. 101, 1–9). Since most obesity generally involves an increase in both cell size and cell number, inhibition of SREBP-1 might be expected to have a positive effect on obesity. The hypolipidemic effects of dietary polyunsaturated fatty acids are believed to derive from a direct inhibitory effect on SREBP-1 expression (Xu et al. (1999) J. Biol. Chem. 274, 23577–23583).

There is data indicating independent regulation of SREBP-1 and SREBP-2 in hamster liver, suggesting the possibility for specific targeting of SREBP-1 or -2 (Sheng et al. (1995) Proc. Natl. Acad. Sci. U.S.A. 92, 935–938).

Transgenic mice over-expressing a dominant-positive form of SREBP-2 in the liver and adipose tissue showed greatly increased levels of mRNAs encoding multiple enzymes of cholesterol synthesis. Enzymes involved in fatty acid synthesis were also increased, however, to a lesser extent (Horton et al. (1998) J. Clin. Invest. 101, 2331–2339). Transgenic mice over-expressing a constitutively active SREBP-1a in the liver and adipose tissue showed greatly increased mRNA levels for enzymes involved in fatty acid and cholesterol (Shimano et al. (1996) J. Clin. Invest. 98, 1575–1584). Their livers were enlarged about 4-fold due to a massive accumulation of free fatty acids and cholesterol. Over-expression of a corresponding version of SREBP-1c in adipocytes of transgenic mice yielded insulin resistance and diabetes (Shimomura et al. (1999) Genes Dev. 12, 3182–3194). In cell culture such overexpression was previously shown to promote adipocyte differentiation. It has further been shown that overnutrition increases SREBP-1c expression in liver and islets of obese fa/fa Zucker diabetic fatty rats (Kakuma, T. et al. (2000) Proc. Natl. Acad. Sci. U.S.A. 97: 8536–8541).

S-1 Protease

As discussed above, SREBPs are activated by proteolysis, which releases the active transcription factor. The luminal subtilisin-like protease Site-1 Protease (S1P) is responsible for the first of the two proteolytic steps. Cleavage by S1P enables further cleavage by a Site-2 protease. S1P is the target for feedback inhibition by cholesterol.

S1P from hamster has been cloned (Sakai et al. (1998) Molecular Cell 2, 505–514). (GenBank accession no. AF078105; SEQ ID NOS: 5 and 6). The corresponding sequence of the (then unidentified) human gene was disclosed by Nagase et al. (1995) DNA Research 2, 37–43 (GenBank Accession no. D420453; SEQ ID NOS: 3 and 4)

SREBP and S1P are co-localized with a third protein: SREBP Cleavage-Activating Protein (SCAP), which is required for Site-1 cleavage in vivo. SCAP contains a site for sterol regulation, conserved in a small number of proteins, e.g. HMG-CoA reductase.

Only one S1P has been identified among the human expressed sequence tags (ESTs). Thus, S1P may be the only member of a subfamily among the subtilisin-like proteases.

Consequently, SREBPs are important regulators of fat and sugar metabolism in mammals and direct or indirect down-regulation of SREBPs may be of therapeutic value in type II diabetes; obesity, hypercholesterolemia, and other cardio-vascular diseases or dyslipidemias.

Site-1 Protease represents a molecular target for therapeutic intervention which is expected to interfere with the SREBP pathway. Two principally distinct concepts for inhibition of the site-1-protease activity may be postulated; (i) by inactivation of the proteolytic activity (classical inhibitors) or (ii) by modulation of the site-1-protease gene expression level. In order to modulate the expression of the site-1-protease gene, there is a need for identification of regulatory regions responsible for the regulation of Site-1 protease promoter. Such regulatory regions in the promoter could be used for the identification of agents that inhibit expression of Site-1 protease, and thereby for the inhibition of the SREBP pathway.

DISCLOSURE OF THE INVENTION

The 5'-flanking region (promoter region) of the human Site-1 Protease (S1P) gene has been cloned and sequenced.

This promoter region is useful in biological assays for the identification of compounds that inhibit the transcription of the Site-1 Protease. Inhibition of the SREBP pathway is expected to have therapeutic value in type II diabetes; obesity, hypercholesterolemia, and other cardiovascular diseases or dyslipidemias.

Consequently, in a first aspect this invention provides an isolated human site-1 protease promoter region comprising a sequence selected from:

(a) the nucleotide sequence set forth as SEQ ID) NO: 2, or a fragment thereof exhibiting site-1 protease promoter activity;

(b) the complementary strand of (a); and (c) nucleotide sequences capable of hybridizing, under stringent hybridization conditions, to a nucleotide sequence as defined in (a) or (b).

The term "promoter region" refers to a region of DNA that functions to control the transcription of one or more genes, and is structurally identified by the presence of a binding site for DNA-dependent RNA polymerase and of other DNA sequences on the same molecule which interact to regulate promoter function.

The nucleic acid molecules according to the present invention includes cDNA, chemically synthesized DNA, DNA isolated by PCR, genomic DNA, and combinations thereof. Genomic DNA may be obtained by screening a genomic library with the cDNA described herein, using methods that are well known in the art.

In a preferred form of the invention, the said nucleic acid molecule has a nucleotide sequence identical with SEQ ID NO: 2 of the Sequence Listing. However, the nucleic acid molecule according to the invention is not to be limited strictly to the sequence shown as SEQ ID NO: 2. Rather the invention encompasses nucleic acid molecules carrying modifications like substitutions, small deletions, insertions or inversions, which nevertheless have S1P promoter activity. Included in the invention are consequently nucleic acid molecules, the nucleotide sequence of which is at least 90% homologous, preferably at least 95% homologous, with the nucleotide sequence shown as SEQ ID NO: 2 in the Sequence Listing.

The term "stringent hybridization conditions" is known in the art from standard protocols (e.g. Ausubel et al., supra) and could be understood as e.g. hybridization to filter-bound DNA in 0.5 M $NaHPO_4$, 7% sodium dodecyl sulfate (SDS), 1 mM EDTA at +65° C., and washing in 0.1×SSC/0.1% SDS at +68° C.

The said "fragment" (partial sequence) exhibiting site-1 protease promoter activity can be identified by the skilled person by computer-assisted sequence analysis, e.g. prediction of transcription factor binding sites.

The invention further provides a recombinant construct comprising the human site-1 protease promoter region as defined above. Preferably, the said construct comprises the S1P promoter region operably linked to a gene encoding a detectable product, in particular the human site-1 protease gene (SEQ ID NO: 3).

The term "linked" indicates that a nucleotide sequence encoding a gene product and an S1P promoter, or an active fragment thereof, are located within a continuous nucleic acid sequence. The term "operably linked" means that a nucleotide sequence, which can encode a gene product, is linked to the S1P promoter such that the S1P promoter regulates expression of the gene product under appropriate conditions. Two nucleotide sequences that are operably linked contain elements essential for transcription, including, for example, a TATA box.

The recombinant construct according to the invention could further comprise a reporter gene. As used herein, the term "reporter gene" means a gene encoding a gene product that can be identified using simple, inexpensive methods or reagents and that can be operably linked to a S1P promoter or an active fragment thereof. Reporter genes such as, for example, a luciferase, β-galactosidase, alkaline phosphatase, or green fluorescent protein reporter gene, can be used to determine transcriptional activity in screening assays according to the invention (see, for example, Goeddel (ed.), Methods Enzymol., Vol. 185, San Diego: Academic Press, Inc. (1990); see also Sambrook, supra).

In another aspect the invention provides a vector comprising the recombinant construct as defined above. The term "vector" refers to any carrier of exogenous DNA that is useful for transferring the DNA to a host cell for replication and/or appropriate expression of the exogenous DNA by the host cell. A host cell stably transformed with the recombinant construct is an additional aspect of the invention. Such a host cell can be a prokaryotic cell, a unicellular eukaryotic cell, or a cell derived from a multicellular organism. The methods employed to effect introduction of the vector into the host cell are standard methods well known to a person familiar with recombinant DNA methods. The term "transformed" or "transfected" refers to the process by which exogenous DNA is transferred into an appropriate host cell.

In a further important aspect, this invention is useful in screening for pharmacological agents that modulate S1P levels by affecting the transcription of the S1P gene. As used herein, the term "agent" means a biological or chemical compound such as a simple or complex organic molecule, a peptide, a protein or an oligonucleotide. Consequently, this invention includes a method for identifying an agent capable of modulating the S1P promoter, comprising providing a cell comprising the S1P promoter; contacting said cell with a candidate agent; and monitoring said cell for an effect that is not present in the absence of said candidate agent.

A preferred form of the invention include a method for identification of an agent capable of decreasing or inhibiting site-1 protease promoter activity, said method comprising the steps (i) contacting a candidate agent with the human site-1 protease promoter; and (ii) determining whether said candidate agent decreases expression of the site-1 protease gene, such decrease being indicative for an agent capable of decreasing or inhibiting site-1 protease promoter activity.

For screening purposes, appropriate host cells can be transformed with a vector having a reporter gene under the control of the human S1P promoter according to this invention. The expression of the reporter gene can be measured in the presence or absence of an agent with known activity (i.e. a standard agent) or putative activity (i.e. a "test agent" or "candidate agent"). A change in the level of expression of the reporter gene in the presence of the test agent is compared with that effected by the standard agent. In this way, active agents are identified and their relative potency in this assay determined.

It will be understood that agents acting on the human S1P promoter can be identified by, as an additional step, analyzing direct binding interactions between the candidate agent and the human S1P promoter. Interactions with large molecules may be studied using techniques such as gel shift analysis, footprinting or NMR (see Latchman, D. S. (Ed.) (1995) Methods for studying transcription factors. In: Eukaryotic transcription factors. Academic Press, London, pp. 17–44). Small molecule compounds which appear to bind reversibly to double stranded DNA without intercalation between DNA base pairs have been defined. Methods are described by which this non-intercalative binding can be characterized using ultraviolet spectrometry, fluorimetry with ethidium as a probe, viscometry and other hydrodynamic techniques, circular dichroism and nuclear magnetic resonance spectrometry (See Baguley, B. C. (1982) Nonintercalative DNA-binding antitumour compounds. Mol Cell Biochem 43: 167–181; Gmeiner, W. H. (1998) NMR spectroscopy as a tool to investigate the structural basis of anticancer drugs. Curr Med Chem 5(2):115–135; Wemmer, D. E. & Williams, P. G. (1994) Use of nuclear magnetic resonance in probing ligand-macromolecule interactions. Methods Enzymol. 239:739–767)

A potentially useful method for identification of agents acting on the human S1P promoter is described in Swedish patent application No. 0101218-6, filed on Apr. 5, 2001. Such a method comprises the steps (a) predicting the structure of an RNA-fragment;
(b) choosing a suitable predicted RNA-fragment of step (a), which RNA-fragment comprises at least one individual stem;
(c) synthesizing the DNA-fragment corresponding to the RNA-fragment of step (b);
(d) inserting the DNA-fragment of step (c) in the upstream proximity of a reporter assay gene, which reporter assay gene produces a signal upon translation, thereby forming a reporter construct;
(e) performing a reporter gene assay, which assay monitors the interaction between a molecule to be tested for RNA-binding and the RNA-fragment of the reporter construct.

As mentioned above, it is expected that agents capable of decreasing or inhibiting site-1 protease promoter activity have potential therapeutic value in particular in obesity, and in type II diabetes; hypercholesterolemia, atherosclerosis and other cardiovascular diseases or dyslipidemias. Consequently, the invention comprises a method for the treatment of medical conditions related to obesity, comprising administering to a patient in need thereof a therapeutically effective amount of an agent identified by the method according to the invention.

The term "treatment" means any treatment of a diseases in a mammal, including: (i) preventing the disease, i.e. causing the clinical symptoms of the disease not to develop; (ii) inhibiting the disease, i.e. arresting the development of clinical symptoms; and/or (iii) relieving the disease, i.e. causing the regression of clinical symptoms. The term "effective amount" means a dosage sufficient to provide treatment for the disease state being treated. This will vary depending on the patient, the disease and the treatment being effected.

Throughout this description the terms "standard protocols" and "standard procedures", when used in the context of molecular biology techniques, are to be understood as protocols and procedures found in an ordinary laboratory manual such as: Current Protocols in Molecular Biology, editors F. Ausubel et al., John Wiley and Sons, Inc. 1994, or Sambrook, J., Fritsch, E. F. and Maniatis, T., Molecular Cloning: A laboratory manual, 2nd Ed., Cold Spring Harbor Laboratory Press, Cold Spring Harbor, N.Y. 1989.

EXAMPLES

Example 1

Cloning of S1P Promoter Fragment

For cloning of the 5'-flanking region of the S1-protease gene, a genomic walking strategy was used, principally as described by Siebert et al. (1995) Nucleic Acids Res. 23,1087–1088; and Siebert et al. (1995) CLONTECHniques X, 1–3. Two primers, designated FOMA 345 and FOMA 346, were selected in the 5'-region of the cDNA:

FOMA 345: 5'-CTC CGC GGC GAA CAC GCCT-3' (corresponding to positions 126–108 in SEQ ID NO: 3);
FOMA 346: 5'-CGG GAG CTC AGG GCC GGC-3' (corresponding to positions 163–146 in SEQ ID NO: 3).

All other reagents used were obtained with a "Genome Walker Kit" (Clontech, Palo Alto, Calif.). The principle of this procedure is to perform two subsequent PCR reactions using adaptor-ligated genomic DNA as template. In the first PCR reaction the "outer" primers are used, i.e. FOMA 345 and AP1 (adaptor primer 1). The protocol for this reaction was:

(+95° for 25 sec; +72° for 4 min)×7 cycles (+95° for 25 sec; +67° for 4 min)×35 cycles (+67° for 4 min)×1 cycle In the second PCR reaction, the "inner" primers were used (FOMA 346 and AP2). The reaction mix from the first PCR was diluted 50 times and 1 $\mu$l of this cocktail was used as template in the second reaction. The protocol of the second reaction was:

(+95° for 25 sec; +72° for 4 min)×5 cycles (+95° for 25 sec; +67° for 4 min)×25 cycles (+67° for 4 min)×1 cycle The reaction mixes were prepared in accordance with the instructions of the kit manufacturer. After the second PCR, the product was analyzed by electrophoresis in 2% agarose gel. A product, approximately 1 kb long, was observed in one of the adaptor-ligated genomic DNA-libraries (HDL2). This product was cloned into the TOPO vector PCR2.1 (Invitrogen, Carlsbad, Calif.) by standard cloning procedures and thereafter sequenced. A 980 bp sequence was obtained (SEQ ID NO: 1).

Example 2

Assembly of S1P Promoter Sequence

The Celera database (Release 1.13) was searched using the 980 bp sequence obtained in Example 1 as query sequence. The BLAST algorithm (Altschul et al. (1997) Nucleic Acids Res. 25:3389-3402) was used for determining sequence identity. Software for performing BLAST analyses is publicly available through the National Center for Biotechnology Information (http://www.ncbi.nlm.nih.gov/). Six fragments (GA_16330554; GA_25791426; GA_23194195; GA_28969362; GA_18902492; GA_24454650) that overlapped with the genomic sequence were retrieved. These six fragments were used to search the Celera database (Release 1.13) again, the overlapping sequences were extended with another 7 fragments (GA_24421404, GA_21984802, GA_28735370, GA_21045430, GA_9491232, GA_13453697, GA_25224137). All 13 fragments together with the 980 bp sequence obtained in Example 1 were finally assembled to a 2469 bp contig (SEQ ID NO: 2) using the Cap2 program (Huang (1996) Genomics 33, 21–31).

Example 3

Reporter Gene Assay to Identify Modulating Compounds

Reporter gene assays are well known as tools to signal transcriptional activity in cells. (For a review of chemiluminescent and bioluminescent reporter gene assays, see Bronstein et al. (1994) Analytical Biochemistry 219, 169–181.) For instance, the photoprotein luciferase provides a useful tool for assaying for modulators of S1P promoter activity. Cells (e.g. CHO cells or COS 7 cells) are transiently co-transfected with both a Site-1 protease expression construct and a reporter construct which includes a gene for the luciferase protein downstream from a transcription factor binding site. Luciferase activity may be quantitatively measured using e.g. luciferase assay reagents that are commercially available from Promega (Madison, Wis.). Differences in luminescence in the presence versus the absence of a candidate modulator compound are indicative of modulatory activity.

A luciferase reporter plasmid is prepared by cloning a 980 bp sequence (SEQ ID NO: 1) corresponding to a part of the site-1-protease promoter into the pGL2 vector, in which the luciferase reporter gene is driven by the activity of the inserted promoter. The construct is thereafter transfected into the mouse pre-adipocyte cell line 3T3-L1 (ATCC No. CCL92.1), the human embryonic kidney cell line 293 (ATCC No. CRL-1573), and the human hepatoma cell line HepG2 (ATCC No. HB-8065). Altered promoter activity after stimulation with a number of substances, including insulin, glitazones and sterols, are measured as changes in the readout of luciferase.

What is claimed is:

1. An isolated human site-1 protease promoter region comprising a sequence selected from:
   (a) the nucleotide sequence set forth as SEQ ID NO: 2 or a fragment thereof exhibiting site-1 protease promoter activity;
   (b) the complementary strand of (a); and
   (c) a nucleic acid sequence that hybridizes to (a) or (b) under conditions of hybridization in 0.5 M NaHPO$_4$, 7% sodium dodecyl sulfite (SDS), 1 mM EDTA at 65° C., and washing in 0.1×SSC/0.1% SDS at 68° C., wherein the nucleic acid exhibits site 1-protease promoter activity.

2. A recombinant construct comprising the human site-1 protease promoter region according to claim 1.

3. The recombinant construct according to claim 2 wherein the human site-1 protease promoter region is operably linked to a gene encoding a detectable product.

4. The recombinant construct according to claim 3 wherein said gene encoding a detectable product is a human site-1 protease gene.

5. The recombinant construct according to claim 2 further comprising a reporter gene.

6. A vector comprising the recombinant construct according to claim 2.

7. A host cell stably transformed with the recombinant construct according to claim 2.

8. A host cell stably transformed with the vector according to claim 6.

9. A vector comprising the recombinant construct according to claim 3.

10. A vector comprising the recombinant construct according to claim 4.

11. A vector comprising the recombinant construct according to claim 5.

12. A host cell stably transformed with the recombinant construct according to claim 3.

* * * * *